United States Patent [19]

Sitzmann et al.

[11] Patent Number: 4,499,309

[45] Date of Patent: Feb. 12, 1985

[54] DERIVATIVES OF ENERGETIC ORTHOFORMATES

[75] Inventors: Michael E. Sitzmann, Adelphi; William H. Gilligan, Fort Washington, both of Md.

[73] Assignee: The United States of America as represented by the Secretary of the Navy, Washington, D.C.

[21] Appl. No.: 467,715

[22] Filed: Feb. 18, 1983

[51] Int. Cl.³ .............................................. C07C 43/32
[52] U.S. Cl. ..................... 568/590; 568/22; 568/595; 149/88; 548/319; 548/320; 260/349; 260/465.6
[58] Field of Search ................................ 568/590, 595

[56] References Cited

U.S. PATENT DOCUMENTS

| | | | |
|---|---|---|---|
| 3,388,147 | 6/1968 | Kamlet et al. | 568/590 |
| 3,407,236 | 10/1968 | Porter | 568/595 |
| 3,415,847 | 12/1968 | Talbot | 568/595 |

*Primary Examiner*—Howard T. Mars
*Attorney, Agent, or Firm*—Robert F. Beers; Kenneth E. Walden; Roger D. Johnson

[57] ABSTRACT

Energetic orthoformates of the formula

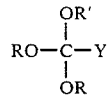

wherein R and R' vary independently and R is
—$CH_2C(NO_2)_2CH_3$,
—$CH_2C(NO_2)_3$,
—$CH_2CF(NO_2)_2$,
—$CH_2CF_2(NO_2)$, or
—$CH_2CF_3$, R' is
—$CH_2CF(NO_2)_2$,
—$CH_2F_2(NO_2)$, or
—$CH_2CF_3$, and Y is —F, —$N_3$, —C≡N,

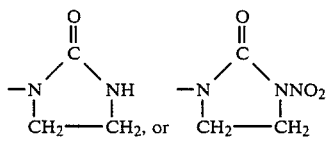

and methods of preparation.

6 Claims, No Drawings

DERIVATIVES OF ENERGETIC ORTHOFORMATES

BACKGROUND OF THE INVENTION

This invention relates to organic orthoformates and more particularly to fluoro-, nitro-, and fluoronitro-substituted organic orthoformates.

In the early 1950's, M. E. Hill and coworkers at the Naval Ordnance Laboratory found that certain nitroalcohols would react with chloroform in the presence of anhydrous ferric chloride to yield

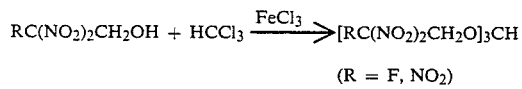

symmetrical orthoformates, (e.g., see U.S. Pat. No. 3,306,939 entitled "Orthoesters of 2,2,2-Trinitroethanol," which issued to Marion E. Hill on Feb. 28, 1967.) However, the reaction is of very limited synthetic value for energetic orthoformates as only two nitroalcohols (2-fluoro-2,2-dinitroethanol and 2,2,2-trinitroethanol) have been successfully used. With other nitroalcohols side reactions predominate. Another drawback to Hill's method is that only symmetrical and no "mixed" orthoformates can be prepared. Moreover, it would be desirable to replace the primary hydrogen with other groups.

SUMMARY OF THE INVENTION

Accordingly, an objective of this invention is to provide novel organic compounds.

Another object of this invention is to provide novel organic orthoformates.

A further object is to provide new high energy, high density explosives.

Yet another object of this invention is to provide new melt castable explosives.

A still further object of this invention is to provide new high energy plasticizers.

Another object of this invention is to provide a new method of synthesizing novel explosive compounds.

This and other objects of this invention are accomplished by providing orthoformates of the formula

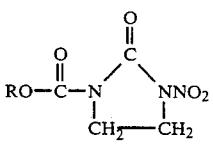

wherein R is
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), or
—CH$_2$CF$_3$,
R' is
—CH$_2$CF(NO$_2$)$_2$,
CH$_2$CF$_2$(NO$_2$), or
—CH$_3$CF$_3$, and
Y is —F, —N$_3$, —C≡N,

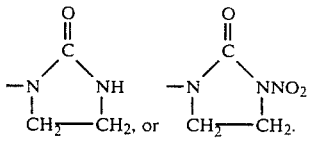

Methods for synthesizing these orthoformates are also disclosed. In addition compounds of the formula

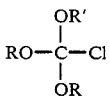

and methods of preparation wherein R is as defined above, are disclosed.

DETAILED DESCRIPTION OF THE PREFERRED EMBODIMENT

The energetic orthoformates of the present invention are prepared by reacting chloroformates of the formula

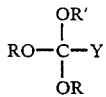

wherein R is
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), or
—CH$_2$CF$_3$, and
R' is
—CH$_2$CF(NO$_2$)$_2$,
CH$_2$F$_2$(NO$_2$), or
—CH$_2$CF$_3$ with one of the following compounds: hydrogen fluoride, potassium or sodium azide, trimethysilyl cyanide, or 2-imidazolidone to produce an orthoformate of the formula

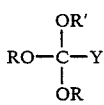

wherein R and R' are as defined above and Y is
—F, —N$_3$, —CN, or

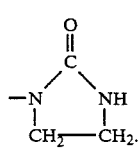

The reaction conditions and methods of preparation are illustrated by examples 6 through 9. Example 6 illustrates the preparation of the fluoroothoformates,

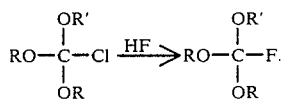

Example 7 illustrates the preparation of the azidoorthoformates,

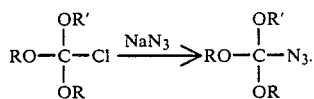

Example 8 illustrates the preparation of the cyanoorthoformates,

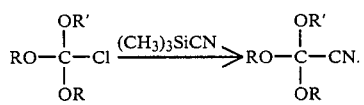

Finally, example 9 illustrates the preparation of the orthoformates containing the imidazolidone group

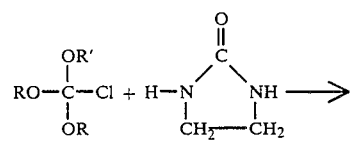

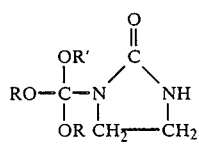

Again, in each of the above reactions, R is
- —$CH_2C(NO_2)_2CH_3$,
- —$CH_2C(NO_2)_3$,
- —$CH_2CF(NO_2)_2$,
- —$CH_2CF_2(NO_2)$, or
- —$CH_2CF_3$ and R' is
- —$CH_2CF(NO_2)_2$
- —$CH_2CF_2(NO_2)$, or
- —$CH_3CF_3$.

Example 10 illustrates that the orthoformates of the formula

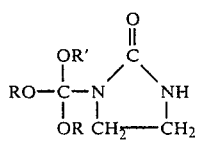

can be nitrated by using 90% nitric acid and concentrated sulfuric acid at 0° C. to produce orthoformates of the formula

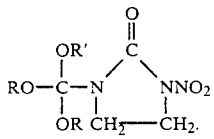

Example 11, illustrates that urethanes of the formula

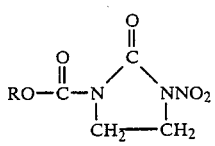

can be prepared from the orthoformates of the formula

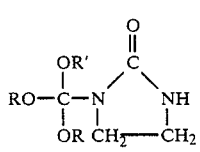

wherein R and R' are the same and are
- —$CH_2CF(NO_2)_2$,
- —$CH_2CF_2(NO_2)$, or
- —$CH_2CF_3$.

The orthoformates are nitrated at about 27° C. (or ambient temperature) using concentrated sulfuric acid and 90% nitric acid to yield urethanes of the formula

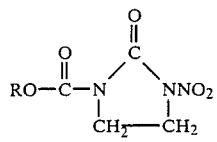

wherein R is as defined above.

The chloroorthoformates used in the above reactions,

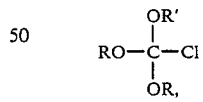

are prepared by dissolving the corresponding disulfides of the formula

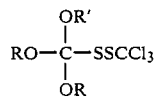

in a suitable solvent (e.g., 1,2-dichloroethane) and then bubbling the chlorine gas into the solution. A preferred reaction temperature is from about 60° C. to about 70° C. Examples 6 through 9 further illustrate this procedure.

The disulfides of the formula $$\begin{array}{c} \text{OR}' \\ | \\ \text{RO}-\text{C}-\text{SSCCl}_3 \\ | \\ \text{OR} \end{array}$$

are prepared by reacting a thionocarbonate of the formula $[RO]_2C{=}S$ with an alcohol of the formula

R'OH and perchloromethyl mercaptan,

ClSCCl$_3$, in the presence of a hydroxyl ion source to produce a disulfide of the formula $(RO)_2(R'O)CSSCCl_3$.

The hydroxyl ions are added slowly so the solution is only slightly basic, having a pH of not more than 8. This is done to avoid the hydrolysis of the thionocarbonates to carbonates which occurs in strongly basic solutions. Again R is
—CH$_2$C(NO$_2$)$_2$CH$_3$,
—CH$_2$C(NO$_2$)$_3$,
—CH$_2$CF(NO$_2$)$_2$,
—CH$_2$CF$_2$(NO$_2$), or
—CH$_2$CF$_3$, and
R' is
—CH$_2$CF(NO$_2$)$_2$,
—CH$_2$CF$_2$(NO$_2$), or
—CH$_2$CF$_3$.

Thus the thionocarbonates used will be
bis(2,2-dinitropropyl)thionocarbonate, [CH$_3$C(NO$_2$)$_2$CH$_2$O]$_2$C=S;
bis(2,2,2-trinitroethyl)thionocarbonate, [C(NO$_2$)$_3$CH$_2$O]$_2$C=S;
bis(2-fluoro-2,2-dinitroethyl)thionocarbonate, [CF(NO$_2$)$_2$CH$_2$O]$_2$C=S;
bis(2,2-difluoro-2-nitroethyl)thionocarbonate, [CF$_2$(NO$_2$)CH$_2$O]$_2$C=S;
and bis(2,2,2-trifluoroethyl)thionocarbonate, [CF$_3$CH$_2$O]$_2$C=S.

Bis(2-fluro-2,2-dinitroethyl)thionocarbonate can be prepared from 2-fluoro-2,2-dinitroethanol and thiophosgene using the method disclosed in U.S. Pat. No. 4,172,088 entitled, "Bis(2-fluoro-2,2-dinitroethyl)thionocarbonate and a Method of Preparation," which issued to Isaac A. Angres et al. on Oct. 23, 1979, herein incorporated by reference. The remaining thionocarbonates can be synthesized from thiophosgene and the appropriate alcohol using the method disclosed in U.S. Pat. No. 4,323,518 entitled "Polynitroethylthionocarbonates and Method of Preparation," which issued to Willian H. Gilligan on Apr. 6, 1982, herein incorporated by reference.

The alcohols used are
2-fluoro-2,2-dinitroethanol; CF(NO$_2$)$_2$CH$_2$OH;
2,2-difluoro-2-nitroethanol, CF$_2$(NO$_2$)CH$_2$OH; and
2,2,2-trifluoroethanol, CF$_3$CH$_2$OH.

Note that the alcohol may be chosen so that either R=R' or R≠R'.

The thionocarbonate, alcohol, and perchloromethyl mercaptan are dissolved in a suitable solvent such as dichloromethane, 1,2-dichloroethane, or 1,1,2-trichloroethane. The reaction occurs as a strong hydroxyl ion source, preferably an alkali metal hydroxide, and more preferably NaOH or KOH, is slowly added so that the pH of the reaction mixture does not exceed 8. The reaction temperature is preferably kept at from about 0° C. to about 5° C. by external cooling, agitation (e.g., stirring), and controlled addition of the hydroxyl ion source. Examples 1 through 5 further illustrate this procedure.

A phase transfer catalyst (e.g., tetrabutyl ammonium chloride) is preferably used to speed up the reactions forming the disulfides. Phase transfer catalysts such as benzyltriethylammonium chloride, tetrabutylammonium chloride, didodecyldimethylammonium bromide, or cetyltrimethylammonium chloride may be used. The phase transfer catalyst is not consumed by the reaction; therefore only a small amount, a few mole percent, of the phase transfer catalyst is required.

Good discussions on the use of phase transfer catalysts are presented by Charles M. Starks, "Phase Transfer Catalysts. I. Heterogeneous Reactions Involving Anion Transfer by Quaternary Ammonium and Phosphonium Salts," Journal of the American Chemical Society, Volume 93: 1, Jan. 13, 1971, pages 195–199, and by Echehard V. Dehmlow, "Phase-Transfer Catalyzed Two-Phase Reactions in Preparative Organic Chemistry," Angew. Chem. internat Edit. volume 13 (1974)/No. 3, Pages 170–178, adapted in Chemtech, April 1975, pages 210–218.

The general nature of the invention having been set forth, the following examples are presented as specific illustrations thereof. It will be understood that the invention is not limited to these examples but is susceptible to various modifications that will be recognized by one of ordinary skill in the art.

EXAMPLE 1

Tris(2-fluoro-2,2-dinitroethoxy)methyl trichloromethyl disulfide from thiophosgene

[CF(NO$_2$)$_2$CH$_2$O]$_3$CSSCl$_3$

A well-stirred mixture of 40 g (0.26 mol) of 2-fluoro-2,2-dinitroethanol in 110 ml of methylene chloride and 2 g of tetrabutyl ammonium chloride in 100 ml of water was cooled in an ice-salt bath to 0° C. A solution of 6.60 g (0.05 mol) of 85% thiophosgene (from Aldrich Chemical Co.; contained 15% carbon tetrachloride) and 12.1 g (0.065 mol) of perchloromethyl mercaptan in 30 ml of methylene chloride was added all at once followed by the dropwise addtion of 11.2 ml of 50% aqueous sodium hydroxide keeping the temperature at 0° to 4° C. The reaction solution was then stirred at 0° C. for 40 minutes keeping it slightly basic by the occasional addition of a few drops of 50% sodium hydroxide. The methylene chloride layer was separated, dried (MgSO$_4$), and the volatiles were removed to give 45.8 g of oily residue which was dissolved in 60 ml of chloroform. Cooling to −20° C. gave 1.55 g (6%) of di[tris(2-fluoro-2,2-dinitroethoxy)methyl]disulfide (XVI). Hexane was added to the chloroform mother liquor until it began to cloud at room temperature. It was then treated with charcoal and filtered through a silica gel pad (40 g silica gel 60; pad was 2.5 inch diameter and 1 inch deep). The pad was washed with 4×50 ml of chloroform-hexane (3:2). Additional hexane was added to the filtrate (to give 350 ml total volume) which was then cooled in dry ice-acetone to give 23.0 g (70%) of white solid, mp 52°–55° C. Recrystallization by dissolving in 50 ml chloroform, adding 75 ml hexane and cooling to −20° gave 21.2 g (65%), mp 55°–57° C.; H-NMR(CDCl$_3$) δ 4.84(d); mass spectrum (C.I.): (m/e)503, 471.

Anal. Calcd. for $C_8H_6N_6F_3Cl_3S_2O_{15}$: C, 14.70; H, 0.93; N, 12.86; F, 8.72; Cl, 16.27; S, 9.81. Found: C, 14.59; H, 1.07; N, 12.64; F, 8.64; Cl, 16.32; S, 9.61.

EXAMPLE 2

Tris(2-fluoro-2,2-dinitroethoxy)methyl trichloromethyl disulfide from Bis(2-fluoro-2,2-dinitroethyl)thionocarbonate

A solution of 17.5 g (0.05 mol) of bis(2-fluoro-2,2-dinitroethyl)thionocarbonate, 17.7 g (0.115 mol) of 2-fluoro-2,2-dinitroethanol and 12.1 g (0.065 mol) of perchloromethylmercaptan in 110 ml of methylene chloride was stirred vigorously in an ice-salt bath. A solution of 2 g of tetrabutyl ammonium chloride in 75 ml of water was added followed by the dropwise addition of 6 ml of 50% aqueous sodium hydroxide with cooling at 2° to 5° C. The reaction solution was kept slightly basic at 0° C. for 20 minutes by occasional addition of a few drops of 50% sodium hydroxide. Workup (same as in example 1) gave 2.79 g (11%) of di[tris(2-fluoro-2,2-dinitroethoxy)methyl]disulfide and 28.3 g (86%) of tris(2-fluoro-2,2-dinitroethoxy)methyl trichloromethyl disulfide, mp 52°–55° C. Recrystallization gave 26.05 g (80%), mp 55°–57° C.

A similar run starting with 42 g (0.12 mol) of the thionocarbonate, 22.4 g (0.12 mol) of perchloromethylmercaptan and 24 g (0.156 mol) of fluorodinitroethanol gave 8.4 g (14%) of di[tris(2-fluoro-2,2-dinitroethoxy)methyl]disulfide and 55.0 g (70%) of tris(2-fluoro-2,2-dinitroethoxy)methyl trichloromethyl disulfide (III), mp 55°–57° C.

EXAMPLE 3

Bis(2,2-dinitropropoxy) (2-fluoro-2,2-dinitroethoxy)methyl trichloromethyl disulfide A mixture of 20.5 g (0.06 mol) of bis(2,2-dinitropropyl)thionocarbonate, 14.5 g (0.078 mol) of perchloromethyl mercaptan and 21.2 g (0.138 mol) of 2-fluoro-2,2-dinitroethanol in 110 ml of methylene chloride was cooled in an ice-salt bath before 3.0 g of tetrabutyl ammonium chloride in 70 ml of water was added. 50% Aqueous sodium hydroxide (10.0 g) was diluted with 30 ml of water and added dropwise at 0° to 4° C. until the reaction solution turned basic to litmus paper. The methylene chloride layer was separated, dried and the solvent was removed to yield an oil which was washed with 200 ml of hexane and then with 200 ml of water. The insoluble oil was chromatographed on silica gel 60 (methylene chloridehexane as eluent) to give 13.4 g (35%) of an oil which turned solid (mp 63°–66° C.) when triturated with hexane; H-NMR [(CD$_3$)$_2$C=O]: δ 5.34 (d,2H), 4.91 (s,4H), 2.39 (s,6H).

Anal. calcd. for $C_{10}H_{12}N_6FCl_3S_2O_{15}$: C, 18.60; H, 1.87; N, 13.01; F, 2.94; Cl, 16.47; S, 9.93. Found: C, 18.80; H, 1.89; N, 12.96; F, 2.93; Cl, 16.50; S, 9.79.

EXAMPLE 4

Bis(2-fluoro-2,2-dinitroethoxy) (2,2,2-trifluoroethoxy)methyl trichloromethyl disulfide A solution of 10.5 g (0.03 mol) of bis(2-fluoro-2,2-dinitroethyl)thionocarbonate, 7.25 g (0.039 mol) of perchloromethyl mercaptan and 6.9 g (0.069 mol) of 2,2,2-trifluoroethanol in 50 ml of methylene chloride was cooled in an ice-salt bath. Tetrabutyl ammonium chloride (1.5 g) in 30 ml of water was added followed by the dropwise addition of a solution of 2.8 g of sodium hydroxide in 5 ml of water with cooling at 0° to 3° C. The methylene chloride layer was separated, dried and the volatiles were removed to give 16.5 g of oil which was extracted with 3×50 ml of boiling hexanes. The cooled extracts were decanted from a small amount of oily precipitate and the solvent was removed to give 6.0 g (33%) of an oil which was nearly pure by TLC analysis. An analytical sample was obtained by column chromatography on silica gel 60 using hexane followed by methylene chloride-hexane as eluent; H—NMR (CDCl$_3$): δ 4.89 (d,4H), 4.15 (q, 2H).

Anal. calcd. for $C_8H_6N_4F_5Cl_3S_2O_{11}$: C, 16.02; H, 1.01; N, 9.34; F, 15.84; Cl, 17.74; S, 10.69.

EXAMPLE 5

Bis(2,2,2-trifluoroethoxy (2-fluoro-2,2-dinitroethoxy)methyl trichloromethyl disulfide To a well-stirred solution of 7.26 g (0.03 mol) of bis(2,2,2-trifluoroethyl)thionocarbonate, 6.14 g (0.033 mol) of perchloromethyl mercaptan and 6.0 g (0.039 mol) of 2-fluoro-2,2-dinitroethanol in 40 ml of methylene chloride cooled in an ice-salt bath was added 1.5 g of tetrabutyl ammonium chloride in 30 ml of water followed by the dropwise addition of 5 ml of 10N aqueous sodium hydroxide at 0° to 5° C. The reaction solution was then kept slightly basic for 15 minutes by the addition of a few drops of aqueous sodium hydroxide when required. The methylene chloride layer was separated and the solvent was removed to give 18.0 g of oil which was dissolved in a small amount of chloroform and passed through a silica gel 60 column with methylene chloride-hexane (30:70) as eluent. The product was 9.95 g (61%) of an oil; H—NMR (CDCl$_3$): δ 4.90 (d,2H), 4.15 (q, 4H).

Anal. calcd. for $C_8H_6N_2F_7Cl_3S_2O_7$: C, 17.61; H, 1.11; N, 5.13; F, 24.38; Cl, 19.49; S, 11.75. Found: C, 17.62; H, 1.05; N, 5.19; F, 24.17; Cl, 19.24; S, 11.56.

EXAMPLE 6

Tris(2-fluoro-2,2-dinitroethyl)fluoroorthoformate

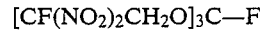

A solution of 6.5 g (0.01 mol) of tris(2-fluoro-2,2-dinitroethoxy)methyl trichloromethyl disulfide in 20 ml of dry 1,2-dichloroethane was treated with dry chlorine gas for 5 hours at ambient temperature. Excess chlorine and approximately one-half of the solvent was removed with a stream of nitrogen and gentle heating before the reaction solution was poured into a teflon bottle containing 5 ml of hydrogen fluoride-pyridine (Aldrich Chemical Co.; contains approx. 70% HF). The mixture was stirred at ambient temperature for 20 hours before it was poured onto ice water and extracted with methylene chloride. Removal of solvent gave a residue which was stirred with hexane to yield 4.54 g (93%) of solid, mp 90°–95° C. Crystallization from chloroform gave 3.88 g (79%), mp 96°–98° C.; H—NMR (CDCl$_3$): δ 4.85 (d); mass spectrum (C.I.): m/e 519(M+C$_2$H$_5$+), 471.

Anal. calcd. for C$_7$H$_6$N$_6$F$_4$O$_{15}$: C, 17.15; H, 1.23; N, 17.15; F, 15.50. Found: C, 17.23; H, 1.33; N, 16.98; F, 15.66.

EXAMPLE 7

Tris(2-fluoro-2,2-dinitroethoxy)azidomethane

[CF(NO$_2$)$_2$CH$_2$O]$_3$C—N—⊖N≡N+

A solution of 2.2 g (0.00336 mol) of tris(2-fluoro-2,2-dinitroethoxy)methyl trichloromethyl disulfide in 6 ml of dry 1,2-dichloroethane at 60° C. was treated with chlorine gas for 2 hours. After an additional 2 hours at 60° C. the volatiles were removed with a stream of nitrogen and the residue was washed three times with hexane to give a solid which was dissolved in 10 ml of dry benzene. Sodium azide (0.45 g, 0.0069 mol) and 18-crown-6 (0.3 g) was added and the mixture was stirred at 25°–27° C. for 20 hours before it was filtered and the filtrate subjected to chromatography on silica gel 60 (methylene chloride-hexane as eluent) to give 1.09 g (63%) of an oil; H—NMR (CDCl$_3$): δ 4.75 (d); IR (liquid film on NaCl plates): 2155 (N$_3$) cm$^{-1}$.

Anal. calcd. for: C$_7$H$_6$N$_9$F$_3$O$_{15}$: C, 16.38; H, 1.18; N, 24.57; F, 11.11. Found: C, 16.52; H, 1.18; N, 24.53; F, 10.91.

EXAMPLE 8

Tris(2-fluoro-2,2-dinitroethoxy)acetonitrile

[CF(NO$_2$)$_2$CH$_2$O]$_3$C—C≡N

Chlorine gas was passed into a solution of 3.3 g (0.005 mol) of tris(2-fluoro-2,2-dinitroethoxy)methyl trichloromethyl disulfide in 10 ml of dry 1,2-dichloroethane at 60° C. for 2 hours. The reaction solution was held at 60° C. for 2 hours before the solvent was removed with a stream of nitrogen and the residue was washed three times with hexane to give a white solid. Dry tetrahydrofuran (10 ml) and trimethylsilyl cyanide (0.75 g, 0.0075 mol) was added and the solution was heated at reflux temperature for 24 hours before the solvent was removed to give a dark oil (2.52 g) which after trituration with chloroform and cooling yielded 1.20 g (48%), mp 73°–75° C.; cystallization from chloroform gave white needles, mp 77°–78° C.; H—NMR [(CD$_3$)$_2$C=O]: δ 5.45 (d); IR (KBr) 2265 (weak) cm$^{-1}$.

Anal. Calcd. for C$_8$H$_6$N$_7$F$_3$O$_{15}$: C, 19.33; H, 1.22; N, 19.72; F, 11.46. Found: C, 19.35; H, 1.22; N, 19.72; F, 11.37.

EXAMPLE 9

1-Tris(2-fluoro-2,2-dinitroethoxy)methyl-2-imidazolidone

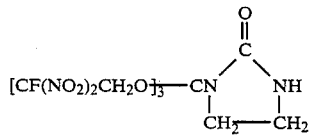

A solution of 19.6 g (0.03 mol) of tris(2-fluoro-2,2-dinitroethoxy)methyl trichloromethyl disulfide in 55 ml of dry 1,2-dichloroethane at 55°–60° C. was treated with chlorine gas for 2 hours, then held at 55°–60° C. for 2 hours before the solvent was removed with a stream of nitrogen. The residue was washed three times with hexane to give a white solid which was dissolved in 60 ml of dry 1,2-dichloroethane. 2-Imidazolidone (6.0 g, 0.069 mol) was added and the mixture was stirred at ambient temperature for 24 hours before the insoluble solid was removed by filtration and stirred with water to give 11.63 g, mp 154°–156° C. Removal of the solvent from the dichloroethane mother liquor (reaction solution) gave a residue which was stirred with chloroform and water to yield an additional 1.12 g, mp 152°–155° C. [total yield=12.75 g (76%)]. The analytical sample from dichloroethane had mp 155°–156° C.; H—NMR(C$_6$D$_6$): δ 4.46 (d, 6H); 4.00 (s, 1H), 2.66 (t, 2H), 2.20 (t, 2H); IR (KBr): 3480 (NH), 1725 (C=O), 1605 (NO$_2$) cm$^{-1}$.

Anal. Calcd. for C$_{10}$H$_{11}$N$_8$F$_3$O$_{16}$: C, 21.59; H, 1.99; N, 20.14; F, 10.25. Found: C, 21.55; H, 2.00; N, 19.96; F, 10.16.

EXAMPLE 10

1-Tris(2-fluoro-2,2-dinitroethoxy)methyl-3-nitro-2-imidazolidone (IV)

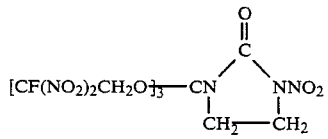

To an ice cold solution of 1 ml of 90% nitric acid and 3.5 ml of concentrated sulfuric acid was added 0.60 g of 1-tris(2-fluoro-2,2-dinitroethoxy)methyl-2-imidazolidone and the mixture was stirred vigorously at 0° C. for 1 hour before it was poured onto ice to give 0.60 g of white solid, mp 187°–195° C. Crystallization from dichloroethane gave 0.42 g (65%) of white crystals, mp 202°–203° C.; H—NMR [(CD$_3$)$_2$C=O]: δ 5.28 (d, 6H), 4.27 (t, 2H), 3.64 (t, 2H); IR (KBr): 1765 (C=O), 1600 with shoulder at 1575 (NO$_2$) cm$^{-1}$.

Anal. calcd. for C$_{10}$H$_{10}$N$_9$F$_3$O$_{18}$: C, 19.98; H, 1.68; N, 20.97; F, 9.48. Found: C, 20.01; H, 1.64; N, 20.72; F, 9.45.

EXAMPLE 11

1-(2-Fluoro-2,2-dinitrocarbethoxy-3-nitro-2-imidazolidone

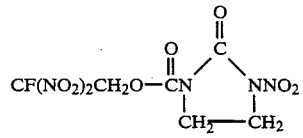

Nitric acid (90%) (6 ml) was combined with 21 ml of concentrated sulfuric acid stirred in an ice bath before 3.0 g of 1-tris(2-fluoro-2,2-dinitroethoxy)methyl-2-imidazolidone was added in portions. The mixture was stirred at 0° C. for 30 minutes and then at 24°–27° C. for 3 hours before it was poured onto ice to give 1.60 g, mp 145°–160° C. Crystallization from dichloroethane gave 1.28 g (76%), mp 162°–166° C. and an additional crystallization from dichloroethane gave the analytical sample, mp 164.5°–166° C.; H—NMR [(CD$_3$)$_2$C=O]: δ 5.64 (d, 2H); 4.28 (t, 2H), 3.91 (t, 2H); IR (KBr): 1820, 1745 (C=O), 1607, 1560 (NO$_2$) cm$^{-1}$; mass spectrum (C.I.): 312 (M+1).

Anal. calcd for $C_6H_6N_5FO_9$: C, 23.16; H, 1.94; N, 22.51; F, 6.11. Found: C, 23.15; H, 1.88; N, 22.16; F, 6.17.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed is:

1. A fluoroorthoformate of the formula

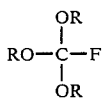

wherein R is selected from the group consisting of
- $-CH_2CF(NO_2)_2$,
- $-CH_2CF_2(NO_2)$, and
- $-CH_2CF_3$.

2. The fluoroorthoformate of claim 1 wherein R is selected from the group consisting of $-CH_2CF(NO_2)_2$ and $-CH_2CF_2(NO_2)$.

3. The fluoroorthoformate of claim 2 which is tris(2-fluoro-2,2-dinitroethyl)fluoroorthoformate.

4. A fluoroorthoformate of the formula

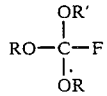

wherein:
(1) $R \neq R'$;
(2) R is selected from the group consisting of
- $-CH_2C(NO_2)_2CH_3$,
- $-CH_2C(NO_2)_3$,
- $-CH_2CF(NO_2)_2$,
- $-CH_2CF_2(NO_2)$, and
- $-CH_2CF_3$; and (3) R' is selected from the group consisting of
- $-CH_2CF(NO_2)_2$,
- $-CH_2CF_2(NO_2)$, and
- $-CH_2CF_3$.

5. The fluoroorthoformate of claim 4 wherein R is selected from the group consisting of
- $-CH_2C(NO_2)_2CH_3$,
- $-CH_2C(NO_3)_3$, and
- $-CH_2CF(NO_2)_2$.

6. The fluoroorthoformate of claim 4 wherein R is selected from the group consisting of
- $-CH_2C(NO_2)_2CH_3$,
- $-CH_2C(NO_2)_3$,
- $-CH_2CF(NO_2)_2$, and
- $-CH_2CF_2(NO_2)$, and wherein R' is selected from the group consisting of
- $-CH_2CF(NO_2)_2$, and
- $-CH_2CF_2(NO_2)$.

* * * * *